(12) United States Patent
Msika et al.

(10) Patent No.: US 9,370,541 B2
(45) Date of Patent: Jun. 21, 2016

(54) EXTRACT OF THE ABOVE-GROUND PORTIONS OF GYNANDROPSIS GYNANDRA OR CLEOME GYNANDRA, AND COSMETIC, DERMATOLOGICAL OR PHARMACEUTICAL COMPOSITIONS INCLUDING SAME

(75) Inventors: Philippe Msika, Versailles (FR); Alex Saunois, Nogent-le-Roi (FR); Caroline Baudouin, Rambouillet (FR); Sophie Leclere-Bienfait, Dreux (FR); Sebastien Debrock, Saint-Martin de Nigelles (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 411 days.

(21) Appl. No.: 13/824,187

(22) PCT Filed: Dec. 22, 2011

(86) PCT No.: PCT/EP2011/073838
§ 371 (c)(1),
(2), (4) Date: Mar. 15, 2013

(87) PCT Pub. No.: WO2012/085230
PCT Pub. Date: Jun. 28, 2012

(65) Prior Publication Data
US 2013/0171082 A1    Jul. 4, 2013

(30) Foreign Application Priority Data

Dec. 22, 2010   (FR) ...................................... 10 61051

(51) Int. Cl.
| | |
|---|---|
| A61K 36/185 | (2006.01) |
| A61K 8/97 | (2006.01) |
| A61K 8/60 | (2006.01) |
| A61Q 19/06 | (2006.01) |
| A61Q 19/08 | (2006.01) |
| A61K 45/00 | (2006.01) |

(52) U.S. Cl.
CPC ............... *A61K 36/185* (2013.01); *A61K 8/602* (2013.01); *A61K 8/97* (2013.01); *A61K 45/00* (2013.01); *A61Q 19/06* (2013.01); *A61Q 19/08* (2013.01); *A61K 2800/805* (2013.01)

(58) Field of Classification Search
USPC ........................................................ 424/725
IPC ..................................................... A61K 36/185
See application file for complete search history.

(56) References Cited

U.S. PATENT DOCUMENTS

| | | | | | |
|---|---|---|---|---|---|
| 4,979,938 | A | * | 12/1990 | Stephen ................... | A61N 1/30 604/20 |
| 6,566,374 | B1 | * | 5/2003 | Keene ................... | A61K 31/451 514/315 |
| 2004/0028643 | A1 | | 2/2004 | Chiba et al. | |
| 2007/0178059 | A1 | * | 8/2007 | Moser ...................... | A61K 8/97 424/74 |
| 2009/0306217 | A1 | * | 12/2009 | Pickett ................... | A01N 49/00 514/688 |
| 2011/0117223 | A1 | * | 5/2011 | Worthington ........ | A61K 31/045 424/742 |
| 2011/0274638 | A1 | * | 11/2011 | Bouix-Peter ......... | A61K 8/4906 424/70.1 |

FOREIGN PATENT DOCUMENTS

| | | | |
|---|---|---|---|
| EP | 1352640 A1 | | 10/2003 |
| JP | 2002179581 | * | 6/2002 |

OTHER PUBLICATIONS

Ajaiyeoba,"Phytochemical and Antimicrobial Studies of Gynandropsis Gynandra and Buchholzia Coriaceae Extracts," African Journal of Biomedical Research vol. 3, 2000, pp. 161-165, XP002651622.

Bala et al., "Evaluation of anticancer activity of Cleome gynandra on Ehrlich's Ascites Carcinoma treated mice," Journal of Ethnopharmacology, vol. 129, 2010, pp. 131-134.

Bellew et al., "Pathogenesis of Acne Vulgaris: What's New, What's Interesting and What May Be Clinically Relevant," The Journal of Drugs in Dermatology, vol. 10, Issue 6, Jun. 2011, pp. 582-585.

Cook et al., "Use of the Trolox Assay to Estimate the Antioxidant Content of Seventeen Edible Wild Plants of Niger," Life Sciences, vol. 63, No. 2, 1998, pp. 105-110.

Ghogare et al., "Antinociceptive activity of Gynandropsis gynandra leaves," Natural Product Research, vol. 23, No. 4, Mar. 2009, pp. 327-333.

Howard et al., "Are There Customary Rights to Plants? An Inquiry Among the Baganda (Uganda), with Special Attention to Gender," World Development, vol. 35, No. 9, 2007, pp. 1542-1563.

(Continued)

*Primary Examiner* — Chris R Tate

(74) *Attorney, Agent, or Firm* — Birch, Stewart, Kolasch & Birch, LLP

(57) ABSTRACT

The invention relates to a composition, such as a cosmetic, dermatological, or pharmaceutical composition, including an extract of the above-ground portions of *Gynandropsis gynandra*, advantageously the leaves and, optionally, a suitable carrier. The invention also relates to such a composition or such an extract to be used in the prevention or treatment of disorders or diseases of the skin, mucous membranes, or nails and hair, to be used in the prevention or treatment of vascular disorders and/or problems linked to hyperseborrhea, or further to be used as an anti-ageing, healing, moisturizing, slimming and/or anti-cellulite, anti-allergy and pro-pigmenting product. Finally, the invention relates to a cosmetic care method for the skin, nails and hair, or mucous membranes, with a view to improving the condition or appearance thereof, consisting of administering such a composition or such an extract.

11 Claims, 1 Drawing Sheet

(56) References Cited

OTHER PUBLICATIONS

Johns et al., "Saponins and phenolic content in plant dietary additives of a traditional subsistence community, The Batemi of Ngorongoro District, Tanzania," Journal of Ethnopharmacology, vol. 66, 1999, pp. 1-10.

Lwande et al., "Gynandropsis gynandra essential oil and its constituents as tick (Rhipicephalus appendiculatus) repellents," Phytochemistry, vol. 50, 1999, pp. 401-405.

Naraendhirakannan et al., "Anti-inflammatory and lysosomal stability actions of Cleome gynandra L. studied in adjuvant induced arthritic rats," Food and Chemical Toxicology, vol. 45, 2007, pp. 1001-1012.

Narendhirakannan et al., "Free radical scavenging activity of Cleome gynandra L. leaves on adjuvant induced arthritis in rats," Molecular and Cellular Biochemistry, vol. 276, 2005, pp. 71-80.

Philippine Medical Plants, "APOI-APOIAN," 2010, retreived from Internet URL:http://www.stuartxchange.org/Apoi-aponian.html, 4 pages, XP002651621.

Sharaf et al., "Exudate Flavonoids from Aerial Parts of Four Cleome Species," Biochemical Systematics and Ecology, vol. 20, No. 5, 1992, pp. 443-448.

Vijayakumar et al., "Antibacterial Activity of Extracts of Cleome gynandra L.," Geobios, vol. 32, 2005, pp. 8-10.

* cited by examiner

EXTRACT OF THE ABOVE-GROUND PORTIONS OF GYNANDROPSIS GYNANDRA OR CLEOME GYNANDRA, AND COSMETIC, DERMATOLOGICAL OR PHARMACEUTICAL COMPOSITIONS INCLUDING SAME

The invention relates to a composition, preferably a cosmetic, dermatological or pharmaceutical composition, including an extract of the above-ground parts of *Gynandropsis gynandra*, advantageously the leaves, and advantageously a suitable carrier.

Advantageously, the extract of the above-ground parts of *Gynandropsis gynandra*, in the composition, has a concentration between 0.01% and 10% by weight in relation to the total weight of the composition.

The invention also relates to a method for extracting an extract of the above-ground parts of *Gynandropsis gynandra* and advantageously the leaves, as well as the extract obtained by said method.

The invention also relates to such a composition or such an extract to be used in the prevention or treatment of disorders or pathologies of the skin, mucous membranes, or keratinous appendages, to be used in the prevention or treatment of vascular disorders and/or problems linked to hyperseborrhea, or to be used as an anti-acne, anti-aging, healing, moisturizing, slimming and/or anti-cellulitis, anti-allergy and pro-pigmenting product. Finally, the invention relates to a cosmetic care method for the skin, keratinous appendages, or mucous membranes, with a view to improving the appearance or condition thereof, consisting of the administration of such a composition or such an extract.

Figure 1:
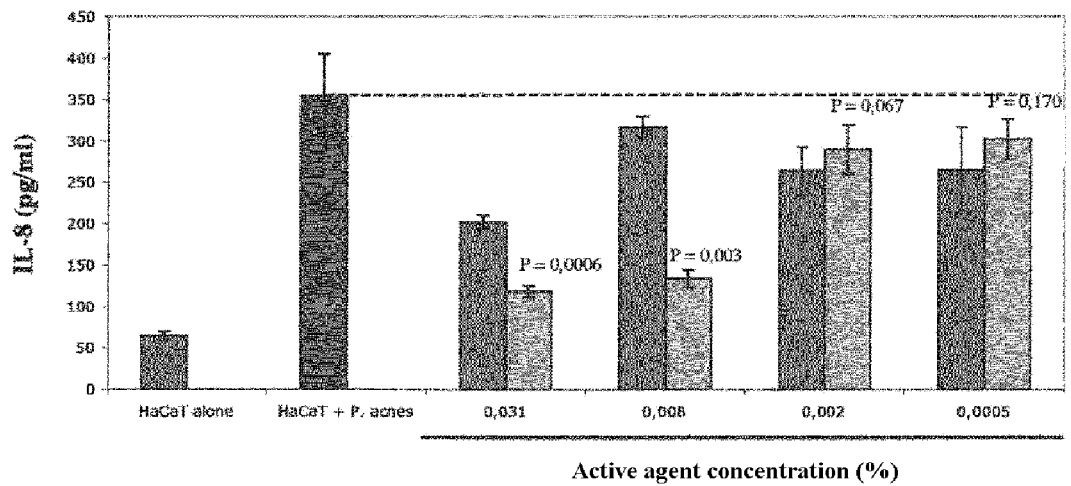
FIG. 1 represents the production of IL8, in pg/ml, by keratinocytes stimulated by *P. acnes*, as a function of the concentration of active agent in percentage.

*Gynandropsis gynandra* is a plant of the family Capparaceae. Its botanical names are *Gynandropsis gynandra* (L.) Briq or *Gynandropsis pentaphylla* or *Cleome gynandra*. It is also referred to various vernacular names, which vary by geographical region. Mention may be made of:

"Wouin wouin" in Jula (southwest Burkina) and "Kyenebdo" in Moré (central Burkina Faso) and many different names in the various African nations;
"Cleome," "Gynandro" and "Mouzambe à fleurs blanches" in French;
"Cat's whiskers" or "spider flower" in English, and
"Senfkapper" and "Benzoinbaun" in German.

It is a small annual herbaceous plant, a crop plant with a height of 15 to 30 cm, capable of reaching 1.5 m in its wild form, with small leaves, round stems, sometimes reddish. Blossoming produces small blue to pale-violet flowers. The fruits are spindle-shaped pods 4 to 6 cm in length containing numerous miniscule, blackish seeds.

The leaves and stems have been described to contain the following compounds:
Isothiocyanate (cleomin),
Sterolic nucleus (lupeol, campesterol, epilupeol),
Vitamin C (127-484 mg/100 g),
β-Carotene (6.7-18.9 mg/100 g),
Carbohydrates (4.4-6.4%),
Proteins (3.1-7.7%),
Phenolic compounds (520-910 mg/100 g),
Calcium (213-434 mg/100 g), and
Magnesium (86 mg/100 g).

The presence of alkaloids is also mentioned by some authors, but not by others.

The leaves and stems have been described to contain the following compounds:
29.5% proteins
28% lipids (59% linoleic acid and about 20% oleic acid)
Sterols
Phenolic compounds (kaempferol, luteolin).

The above-ground parts (stem and leaves) are traditionally used for administration by oral route. Considering its reputation as a plant with a high concentration of vitamins and micronutrients, it is most often used as an edible plant, equally suitable for children and adults and highly recommended during pregnancy, as a condiment for sauces and, most commonly, also as vegetables in soups.

The above-ground parts and oil cakes obtained after extraction of the oil from the seeds may be used as fodder for cattle.

Furthermore, preparations of the leaves, stems and seeds would have insecticidal, vermifugal, antiparasitic and antimicrobial and antioxidant properties when they are consumed orally. The juice of the leaves is used in eye washes. The seeds, which are consumed orally, have antiemetic properties.

In various traditional medicines (in particular in Africa and India), the plant is taken, mainly by oral route, for the treatment of pain (headaches, childbirth pain, stomach pain) and scorpion stings. The leaves may be applied directly to purulent wounds to prevent the formation of pus.

Recent pharmacological studies have supported some of these traditional uses: analgesic activity in mice by intraperitoneal injection of plant extracts (U. R. Ghogare et al., Natural Product Research, 23 (4): 327-333 (2009)); anti-arthritis effect in rats by oral route (R. T. Narendhirakannan et al., Molecular and Cellular Biochemistry, 276: 71-80 (2005)); beneficial cholesterol lowering effect by oral route (T. Johns, Journal of Ethnopharmacology, 66: 1-10 (1999)).

Furthermore, the American application US 2004/0028643A1 describes the screening of numerous plants, to be used in anti-aging compositions. The results given in the examples of this American application indicate that the extract of the *Cleome gynandra* plant (the methanolic extract of an undefined portion or the totality of the plant) does not provide satisfactory results. In particular, following the test of anti-DPPH activity, it was determined that the extract did not exhibit significant activity.

On the contrary, the inventors have discovered that extracts of the above-ground parts (leaves, stems, flowers, seeds) of *Gynandropsis gynandra*, and advantageously extracts of the leaves, exhibited cosmetic and dermatological properties never described to date. The following examples show that the extract of the invention exhibits a significant anti-DPPH activity.

This is the first time that extracts of the above-ground parts of *Gynandropsis gynandra* have been used as such, for their specific properties.

One object of the invention is a composition that includes as an active ingredient an extract of the above-ground parts of *Gynandropsis gynandra* (hereafter called the extract of the invention), advantageously an extract of *Gynandropsis gynandra* leaves, characterized in that the extract includes at least 3% polyphenols by weight, expressed in gallic acid equivalents in relation to the weight of the dry extract.

Advantageously, the polyphenols are flavonoids. According to this special characteristic, the extract includes at least 1% flavonoids by weight, advantageously at least 3% by weight, expressed in rutin equivalents in relation to the weight of the dry extract.

The extract of *Gynandropsis gynandra* of the invention is optionally in combination with a suitable carrier in the composition.

The composition is advantageously a cosmetic, dermatological or pharmaceutical composition.

The composition is advantageously intended to be applied topically to the skin, keratinous appendages and/or mucous membranes, in particular skin, keratinous appendages and/or mucous membranes that are sensitive or damaged by the environment, for example by UV radiation or pollution.

The extract is advantageously an extract of *Gynandropsis gynandra* leaves.

The extract of the invention may be characterized by its polyphenols concentration (Folin-Ciocalteu assay) which is at least 3% by weight expressed in gallic acid equivalents in relation to the weight of the dry extract.

Among the polyphenols present in this extract, flavonoids are of particular interest. Thus, in one advantageous embodiment of the invention, the extract according to the invention may be characterized by its flavonoid content (aluminum chloride assay), which is at least 1% flavonoids by weight expressed in rutin equivalents in relation to the weight of the dry extract. These flavonoids are preferentially mainly composed of rutin and derivatives thereof.

Rutin is a compound of formula (I):

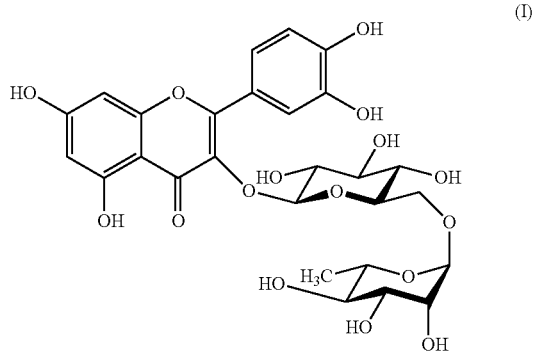

(I)

Rutin derivatives are advantageously compounds in which the flavonic residue of rutin is found, namely the residue of formula (II):

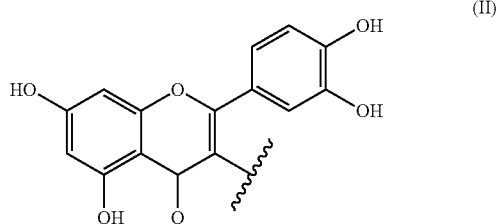 [SMILES: *C1=C(c2ccc(O)c(O)c2)Oc2cc(O)cc(O)c2C1O]

(II)

In the flavonoids contained in the extract of the invention, rutin and derivatives thereof are advantageously found in a proportion, by weight expressed in rutin equivalents in relation to the total flavonoids content by weight, of at least 50%, advantageously at least 60%, more advantageously at least 70%, even more advantageously at least 80%.

According to an advantageous embodiment of the invention, the extract contains from 0 to 80%, advantageously from 10 to 80%, more advantageously from 30 to 70% sugars, percentages being expressed by weight in relation to the weight of the dry extract.

The extract of the invention advantageously contains 0 to 50% by weight, more advantageously 0 to 20% by weight, even more advantageously 0 to 10% by weight of *Gynandropsis gynandra* lipids, percentages being expressed by weight in relation to the total weight of the dry extract.

The extract of the invention advantageously contains 0 to 60% by weight, more advantageously 0.5 to 30% by weight, even more advantageously 0.5 to 10% by weight of *Gynandropsis gynandra* proteins, percentages being expressed by weight in relation to the total weight of the dry extract (Bradford assay).

This extract is advantageously obtained by solid-liquid extraction of the fresh or dried above-ground parts of *Gynandropsis gynandra* in an aqueous and/or alcoholic and/or glycolic and/or glycerolic solvent. The above-ground parts are advantageously the leaves.

The solvent is advantageously selected from the group consisting of water, ethanol, glycerol, a glycol such as propanediol, and mixtures thereof such as binary mixtures, in proportions between 0 and 100% water in relation to the other solvents, more advantageously in proportions between 10 and 50% water in relation to the other solvents.

Predominantly, binary mixtures of solvents of the type consisting of water and one solvent selected from ethanol, glycerol and propanediol are used.

More particularly, between 0.1 and 50% by weight (in dry matter equivalents) of the desired parts of the plant will be introduced into the extraction solvent, and preferentially between 1 and 10% by weight, advantageously 5% by weight (percentages are expressed by weight of the dry matter in relation to the total weight used). The dried portion of *Gynandropsis gynandra* may be the leaves, stems, flowers, seeds, alone or combined, and preferentially the leaves.

In the presence of ethanol, a proportion between 0 and 100% of ethanol in water, preferentially 10 to 80% of ethanol, and advantageously between 60 and 80% will be selected (percentages are expressed by weight of ethanol in relation to the total weight of water+ethanol).

In the presence of glycerol, a proportion between 0 and 100% of glycerol in water, preferentially between 30 and 80%, and advantageously 80% will be selected (percentages are expressed by weight of glycerol in relation to the total weight of water+glycerol).

In the presence of glycol, and more particularly of propanediol, a proportion between 0 and 100% of propanediol in water, preferentially between 10 and 80%, and advantageously 60% will be selected (percentages are expressed by weight of propanediol in relation to the total weight of water+propanediol).

The extraction temperature is advantageously between 4 and 100° C., and preferentially between 10 and 60° C., and more particularly between 15 and 30° C.

The extraction time varies advantageously from 30 minutes to 4 hours, and preferentially 30 minutes to 2 hours, and more advantageously it is about 1 hour.

At the end of the extraction, the residual dry matter is advantageously separated from the liquid phase, for example by filtration, settling or centrifugation. The liquid phase thus obtained may be filtered through filters of suitable pore size in order to obtain a clear solution.

These first separation steps may be followed by purification steps, for example by ultrafiltration and/or nanofiltration, making it possible to concentrate the molecules of potential interest at the expense of others.

The extract obtained may be provided in liquid form but also may be dried according to methods known to the person skilled in the art, for example atomization or freeze-drying with or without a support such as maltodextrin.

Another object of the invention is a method for the preparation of an extract of the above-ground parts of *Gynandropsis gynandra* including the following successive steps:

(a) liquid-phase dispersion in a suitable solvent of the above-ground parts of *Gynandropsis gynandra*, and advantageously the leaves;

(b) subjection of the mixture obtained following step (a) to extraction in an aqueous and/or alcoholic and/or glycolic and/or glycerolic solvent;

(c) centrifugation and/or filtration of the extract obtained following step (b);

(d) if need be, ultrafiltration and/or diafiltration and/or nanofiltration of the extract obtained following step (c);

(e) following step (c) or (d), recovery of the extract of the above-ground parts of *Gynandropsis gynandra*;

(f) optional drying of the extract obtained in step (e) on or not on a support.

During step (a), the leaves are advantageously used in the following proportions: between 0.1 and 50% dry leaf matter, preferentially between 5 and 20%, and advantageously 5%, the percentages being expressed by weight of the dry matter in relation to the total weight used.

Step (b) takes place advantageously under stirring. No enzyme has to be added.

During step (c), the following solvents alone or in mixture with water are advantageously used: ethanol, glycerol or propanediol, in a proportion advantageously between 30 and 90% of these solvents in water, and more advantageously between 50 and 80% (percentages are expressed by weight of the solvent in relation to the total weight of solvent+water).

The extract is advantageously used as an active agent in a composition such as a cosmetic, dermatological or pharmaceutical composition, which may include one or more suitable carriers. The composition may further include at least one other active compound in addition to the extract of the above-ground parts of *Gynandropsis gynandra*. This other compound may be selected from all the compounds and functional equivalents thereof set forth below.

This other compound may be in particular selected from the active agents classically used in dermatology, pharmacology or cosmetics and known to the person skilled in the art, such as emollients, moisturizing active agents, keratoregulators, keratolytics, healing agents and/or agents for restructuring the cutaneous barrier, PPAR, RXR or LXR agonists, sebum-regulating agents, anti-irritation and/or anti-inflammatory and/or soothing agents, antioxidant agents, anti-aging agents, depigmenting or hypopigmenting agents, pigmenting agents, lipolytic or lipogenesis inhibitor agents or anti-cellulitis or slimming agents, organic or mineral sun screens and filters, antifungal compounds, preservatives, antibacterial agents, prebiotics and probiotics, antibiotics, and immunomodulators.

More particularly, the agents for cicatrising and/or restructuring the cutaneous barrier that may be used in combination are advantageously panthenol (vitamin B5), arabinogalactan, zinc oxide, ceramides, cholesterol, squalane and phospholipids.

The sebum-regulating agents that may be used in combination are advantageously selected from the group consisting of 5-alpha reductase inhibitors. Zinc (and zinc derivatives such as gluconate, salicylate salts thereof and pyroglutamic acid) and spironolactone also have sebum-suppressing activity. Other sebum-regulators of lipid origin acting on sebum quality, such as linoleic acid, are also of interest.

The anti-inflammatory and/or anti-irritation and/or soothing agent may be arabinogalactan.

The sun protection active agents that may be used in combination are advantageously UVB and/or UVA filters or sun screens, such as the mineral and/or organic screens or filters known to the person skilled in the art, who will adapt their choice and their concentrations according to the degree of protection sought.

The preservatives that may be used in combination are, for example, those generally used in cosmetics, molecules with antibacterial activity (pseudo-preservatives) such as caprylic derivatives like, for example, capryloyl glycine and glyceryl caprylate; hexanediol, sodium levulinate, and copper and zinc derivatives (gluconate and PCA).

Among the recommended active agents in combination with the extract of the invention, mention may be made of plant extracts, in particular:

plant oils such as soy oil and/or rapeseed oil, avocado oil (WO2004/012496, WO2004/012752, WO2004/016106, WO2007/057439), lupin oil, advantageously sweet white lupin oil (WO 98/47479), or a mixture of these oils;

oleodistillates or concentrates of animal or plant oil, notably sunflower, more advantageously linoleic sunflower concentrates, such as the sunflower oil concentrated in unsaponifiables (Soline®) (see the international application WO 01/21150) marketed by Laboratoires Expanscience, oils concentrated in unsaponifiables as avocado oil, rapeseed oil, corn oil or palm oil, useful notably for their moisturizing and/or emollient, healing and/or restructuring the cutaneous barrier, anti-inflammatory and/or anti-irritation and/or soothing activity;

unsaponifiables of plants or of plant oil, advantageously of avocado furans (Avocadofurane®), able to be obtained by the method described in the international application WO 01/21605, unsaponifiables of avocado and/or soy, more particularly a mixture of furanic unsaponifiables of avocado and unsaponifiables of soy, advantageously in a respective ratio of about 1/3-2/3 (such as Piascledine®), unsaponifiables of soy (such as obtained according to the method described in the international application WO 01/51596), sterolic unsaponifiables (typically unsaponifiables whose proportion of sterols, methylsterols and triterpene alcohols is between 20 and 95% by weight, preferably 45-65% by weight, in relation to the total weight of the unsaponifiable), phytosterols, esters of sterols and vitamin derivatives, notably useful for their healing and/or restructuring the cutaneous barrier, anti-aging, anti-inflammatory activity;

peptides or complexes of plant amino acids, in particular of avocado peptides (such as those described in the international application WO2005/105123), lupin peptides (such as those obtained according to the method described in the application WO2005/102259), quinoa peptides (such as those described in the international application WO2008/080974), maca peptides (such as those described in the international application WO2004/112742), fermented or non-fermented soy peptides, rice peptides (such as those described in the international application WO2008/009709), useful notably for their moisturizing and/or emollient activity (avocado), keratoregulating activity (lupin, quinoa), healing and/or restructuring the cutaneous barrier activity (maca, quinoa, soy), anti-inflammatory and/or anti-irritation and/or soothing activity (lupin, quinoa), antioxidant activity (avocado), anti-aging activity (lupin, maca), pigmenting activity (rice), *Schisandra* peptides (such as those described in the patent application FR 0955344), extract of seeds of *Acacia macrostachya* (such as that described in the patent application FR 0958525) and extract of seeds of *Vigna unguiculata* (such as that described in the patent application FR 0958529);

plant sugars, in particular avocado sugars (such as those described in the application WO2005/115421), useful notably for their keratoregulator, healing and/or restructuring the cutaneous barrier, anti-inflammatory and/or anti-irritation and/or soothing property;

butyl avocadate (5 alpha Avocuta®), 5-alpha reductase inhibitor (see WO 01/52837 and WO 02/06205) and typically, regulator of the seborrheic secretions found increased in acne and in dandruff;

polyphenol-rich extracts, and more particularly extracts of avocado fruits (such as those described in the application FR 1 061 055) and extracts of maca leaves (such as those described in the application FR 1 061 047);

lupeol (FR 2 822 821, FR 2 857 596) useful notably to promote healing;

total extract of lupin (such as those described in the international application WO2005/102259), particularly suitable for the treatment of irritations;

cupuaçu butter, particularly appreciated for its moisturizing properties.

Among the recommended active agents in combination with the extract of the invention, mention may be made of oxazolines, in particular those selected from the group comprised of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline, preferably 2-undecyl-4,4-dimethyl-1,3-oxazoline (OX-100 or Cycloceramide®; WO2004050052, WO2004050079 and WO2004112741). They are particularly useful for their anti-inflammatory and/or anti-irritation and/or soothing, antioxidant, depigmenting, immunomodulatory activity.

Among the active agents recommended in combination with the extract of the invention, mention may be made of 5-alpha reductase inhibitors such as butyl avocadate (5 alpha Avocuta®).

All of these combinations include at least one other active compound, in addition to the extract of the above-ground parts of *Gynandropsis gynandra*, and may include two, three, four or more active compounds as described above.

The composition of the invention may be formulated in the form of various preparations suitable for topical administration, for oral, rectal, vaginal, nasal, auricular or bronchial administration, as well as for parenteral administration. The composition of the invention is advantageously formulated in the form of various preparations suitable for topical administration, more particularly for application on the skin and/or keratinous appendages and/or mucous membranes.

According to a first variant, the various preparations are suitable for topical administration and notably include creams, emulsions, milks, pomades, lotions, oils, aqueous or water-alcoholic or glycolic solutions, powders, patches, sprays, shampoos, varnishes or any other product for external application.

The modes of administration, dosing schedules and optimal galenic forms of the compounds and compositions of the invention may be determined according to the criteria generally taken into account in the establishment of a pharmaceutical treatment, in particular a dermatological, cosmetic or veterinary treatment suitable for a patient or an animal, such as for example the age or the body weight of the patient or animal, the severity of the general condition of the patient or animal, tolerance to the treatment, noted side effects, skin type. Depending on the type of administration desired, the composition and/or active compounds of the invention may further include at least one pharmaceutically acceptable carrier, in particular a dermatologically acceptable carrier, or a cosmetically acceptable carrier. According to the first variant, a carrier suitable for administration by external topical route is used. The composition of the present invention may further include at least one pharmaceutical or cosmetic adjuvant known to the person skilled in the art, selected from thickeners, preservatives, fragrances, colorants, chemical or mineral filters, moisturizing agents, thermal waters, etc.

The composition including an extract of the above-ground parts of *Gynandropsis gynandra* having the specifications indicated is particularly intended for a cosmetic or dermatological use. The composition will be advantageously formulated in the form of a preparation suitable for topical administration.

Another object of the invention is the composition of the invention or an extract of the above-ground parts of *Gynandropsis gynandra* as defined above, to be used as a cosmetic, pharmaceutical or dermatological composition, advantageously a cosmetic or dermatological composition.

Advantageously, the composition or extract of the present invention is used in the prevention and/or treatment of disorders or pathologies of the skin and/or mucous membranes and/or keratinous appendages.

In particular, the composition or extract of the present invention is used in the prevention and/or treatment of disorders related to acne.

The physiopathology of acne is associated with various triggering factors, including hyperseborrhea, follicular hyper-keratinization (comedogenesis) and bacterial colonization by *Propionibacterium acnes* (*P. acnes*). These factors are intricated and interact together (Bellew et al. 2011, 10(6): 582-585).

The production of sebum by sebaceous glands plays a crucial role in the development of acne. Indeed, hyperseborrhea associated with a qualitative change of the sebum generates signals that can induce hyper-keratinization and thus create an environment favorable to the multiplication of *P. acnes*.

Acne is also associated with an excessive development of *P. acnes*. This commensal bacterium acts as an opportunistic pathogen favored by the acne environment (hyperseborrhea, inflammation, follicle obstruction). *P. acnes* produces numerous factors that contribute to aggravate comedogenesis and inflammation: signaling via Toll-like receptors (TLRs) to induce and maintain inflammation, release of enzymes leading to rupture of the follicle wall, production of chemotactic factors to attract the neutrophil.

The composition or extract of the present invention is thus also used in the prevention and/or treatment of disorders related to hyperseborrhea, such as seborrheic dermatitis (cradle cap), acne and skin with acneic tendencies, and dandruff.

The composition or extract of the invention is particularly useful in the prevention and/or treatment of vascular disorders, for the protection of blood vessels and/or to act on the blood circulation, in particular blood microcirculation.

The composition or extract of the invention is thus advantageously used in the prevention and/or treatment of (chronic) dilatation of the subcutaneous capillaries, which may occur under conditions such as couperosis, cutaneous erythema, rosacea, pruritus, reactive skin and/or mucous membranes, with redness, in particular due to dilatation of the subcutaneous capillaries.

The composition or extract of the invention is also advantageously used as a chronological or photo-induced anti-aging product in the prevention of aging, and of photo-induced aging and, as a healing product, in the prevention and/or treatment of disorders related to cicatrization and cutaneous organization.

The expression "disorders related to cicatrization and cutaneous organization" refers to disorders resulting from the processes of cicatrization and cutaneous organization of the skin such as loose skin, stretch marks, scurf, chapping, cracks in particular on the breasts.

In particular, the composition or extract of the invention is used as a moisturizing product, intervening in the prevention and/or treatment of disorders of the barrier or homeostasis of the skin, keratinous appendages (hair and nails) and/or mucous membranes (gums, periodontium, genital mucosa), whether immature, normal or mature/aged.

The expression "disorders of the barrier of the skin, keratinous appendages and/or mucous membranes" refers to disorders intervening at the level of the external layer of the skin.

The expression "disorders of the homeostasis of the skin, keratinous appendages and/or mucous membranes" refers to disorders resulting from the processes of cell renewal and equilibrium such as psoriasis, diaper rash, atopic dermatitis, dry skin (xerosis), dehydrated skin and photosensitive skin.

The composition or extract of the invention is also advantageously used in the treatment and/or prevention of inflammation due to rays of all kinds, in particular sunburn.

The composition or extract of the present invention may be also advantageously used as a slimming product in the regulation of adipose tissue, cellulitis and more particularly via the inhibition of lipogenesis.

The composition or extract of the invention is used as an anti-allergy product in the prevention and/or treatment of reactions or allergic pathologies such as allergic dermatitis, contact dermatitis, eczema and pruritus.

Advantageously, the composition or extract of the invention may be used as a pro-pigmenting product in the prevention and/or treatment of reactions, disorders or pathologies of the skin exhibiting disorders of depigmentation, such as depigmented skin (vitiligo).

Advantageously, the composition or extract of the invention may be used for the prevention and/or treatment of reactions, disorders or pathologies of the skin; or reactions, disorders or pathologies of the keratinous appendages such as those of the hair (alopecia, dandruff, hirsutism, folliculitis); or reactions, disorders or pathologies of the mucous membranes such as the gums and periodontium presenting gingivitis (sensitive gums of newborns, problems of hygiene due to tobacco use or other), periodontopathies or genital mucosa presenting irritations of the external or internal male or female genitalia, related to a deficit in innate immunity (anti-microbial peptides) or acquired immunity (cellular, humoral, cytokines).

The invention also relates to a cosmetic care method for the skin and/or keratinous appendages and/or mucous membranes, with a view to improving the condition and/or appearance thereof, consisting of applying to the skin and/or keratinous appendages and/or mucous membranes of patients in need a composition or extract of the present invention.

In one embodiment of the cosmetic method of the invention, the intended skin and/or keratinous appendages and/or mucous membranes are advantageously those that are sensitive, irritated or damaged by the environment (UV, pollution), in particular sensitive skin. Sensitive skin often has redness (notably facial skin), typically with daily tugging or tingling.

The cosmetic method of the invention is in particular with a view to improving patients suffering from acne and presenting skin with acneic tendency and also with a view to improving dandruff.

The cosmetic method of the invention is also characterized in that the composition or extract is an anti-chronological or photo-induced anti-aging, moisturizing, slimming and/or anti-cellulitis product.

EXAMPLE 1

The dried and crushed leafy stems of *Gynandropsis gynandra* are suspended under stirring at a concentration of 5% in an 80/20 (w/w) ethanol/water mixture for 1 hour at room temperature. The residual dry matter is separated from the liquid phase by filtration, settling or centrifugation and the liquid phase thus obtained may be filtered using filters of suitable pore size in order to obtain a clear solution. The extract obtained has the following characteristics:

Total sugars (anthrone): 41%/dry
Total polyphenols (Folin-Ciocalteu); gallic acid equivalents: 7.7%/dry
Proteins (Bradford assay): 3.1%/dry.

This extract has anti-radical activity, "in tubo" anti-DPPH activity, for which the half maximal inhibitory concentration ($IC_{50}$) could be determined and is 0.2 mg of dry extract, which represents 19 µg of polyphenols in the reaction medium.

EXAMPLE 2

The dried and crushed leafy stems of *Gynandropsis gynandra* are suspended under stirring at a concentration of 5% in an 80/20 (w/w) glycerol/water mixture for 1 hour at room temperature. The residual dry matter is separated from the liquid phase by filtration, settling or centrifugation and the liquid phase thus obtained may be filtered using filters of suitable pore size in order to obtain a clear solution. The extract obtained has the following characteristics:

Total sugars (anthrone): 65%/dry
Total polyphenols (Folin-Ciocalteu); gallic acid equivalents: 6.4%/dry
Flavonoids content ($AlCl_3$); rutin equivalents: 4%/dry
Proteins (Bradford assay): 4.0%/dry.

This extract has anti-radical activity, "in tubo" anti-DPPH activity, for which the half maximal inhibitory concentration ($IC_{50}$) could be determined and is 0.09 mg of dry extract, which represents 7.1 µg of polyphenols in the reaction medium.

EXAMPLE 3

The dried and crushed leafy stems of *Gynandropsis gynandra* are suspended under stirring at a concentration of 5% in a 60/40 (w/w) propanediol/water mixture for 1 hour at room temperature. The residual dry matter is separated from the liquid phase by filtration, settling or centrifugation and the liquid phase thus obtained may be filtered using filters of suitable pore size in order to obtain a clear solution. The extract obtained has the following characteristics:

Total sugars (anthrone): 32%/dry

Total polyphenols (Folin-Ciocalteu); gallic acid equivalents: 7.6%/dry

Flavonoids content ($AlCl_3$); rutin equivalents: 4.8%/dry

Proteins: 1%.

This extract has anti-radical activity, "in tubo" anti-DPPH activity, for which the half maximal inhibitory concentration ($IC_{50}$) could be determined and is 0.16 mg of dry extract, which represents 14 μg of polyphenols in the reaction medium.

EXAMPLE 4

Compositions for Topical Application

The inventors present below several compositions for topical application. The extracts of the above-ground parts of *Gynandropsis gynandra* may be incorporated in various cosmetic products such as cleansing water, oil-in-water emulsions, water-in-oil emulsions, oils, milks, lotions, shampoos, foaming products and sprays, whose compositions are presented below. The percentages represent the weight of the product in relation to the total weight of the composition.

| CLEANSING WATER FOR SENSITIVE SKIN | |
|---|---|
| Brand or INCI name | % |
| CAPRYLOYL GLYCINE | 0-1% |
| LYE SODA | 0-1% |
| SEQUESTRANT | 0-1% |
| BUTYLENE GLYCOL | 1-5% |
| BETA-CAROTENE | 0-2% |
| Extract of *Gynandropsis gynandra* | 0.01-10% |
| PRESERVATIVES | 0-1% |
| PEG-32 | 1-5% |
| PEG-7 PALMCOCOATE | 1-5% |
| ZINC GLUCONATE | 0-1% |
| CITRIC ACID | 0-1% |
| PURIFIED WATER | Q.S. to 100% |
| FRAGRANCE | 0-1% |
| POLOXAMER 184 | 1-5% |

| ANTI-AGING EMULSION | |
|---|---|
| Brand or INCI name | % |
| LIQUID ISOPARAFFIN | 5-20% |
| ISOCETYL STEARATE | 5-20% |
| AL—MG HYDROXYSTEARATE | 5-20% |
| ABIL WE 09 | 1-5% |
| GLYCEROL | 1-5% |
| VASELINE OIL | 1-5% |
| MICRONIZED ZINC OXIDE | 1-5% |
| BUTYLENE GLYCOL | 1-5% |
| RETINOL | 0-1% |
| VITAMIN C | 0-5% |
| Extract of *Gynandropsis gynandra* | 0.01-10% |
| ISONONYL ISONONANOATE | 1-5% |
| BEESWAX | 1-5% |
| SODIUM TARTRATE | 1-5% |
| SODIUM CHLORIDE | 0-5% |
| GLYCINE | 1-5% |
| PRESERVATIVES | 0-1% |
| CHOLESTEROL | 0-1% |
| PHYTOSPHINGOSINE | 0-1% |
| TARTARIC ACID | 0-1% |
| PURIFIED WATER | Q.S. to 100% |

| ANTI-REDNESS EMULSION | |
|---|---|
| Raw material/Brand or INCI name | % |
| PEG 40 STEARATE | 1-5% |
| PEG 5 GLYCERYL STEARATE | 1-5% |
| CERESIN WAX | 1-5% |
| GLYCEROL MONOSTEARATE | 1-5% |
| SORBITAN STEARATE | 0-2% |
| CETYL ALCOHOL | 0-2% |
| DIMALATE ALCOHOL | 5-20% |
| ESCULOSIDE | 0-2% |
| *SOPHORA JAPONICA* | 0-5% |
| VITAMIN E | 0-1% |
| Extract of *Gynandropsis gynandra* | 0.01-10% |
| BUTYLENE GLYCOL | 1-5% |
| PIROCTOLAMINE | 0-1% |
| PRESERVATIVES | 0-1% |
| GLYCEROL | 1-10% |
| XANTHAN GUM | 0-1% |
| ZINC PCA | 0-2% |
| RICE STARCH | 1-5% |
| NYLON 6 | 0-2% |
| POLYACRYLAMIDE GEL | 1-5% |
| VITAMIN B6 | 0-1% |
| FRAGRANCE | 0-1% |
| PURIFIED WATER | Q.S. to 100% |

| SPF 50+ SUN SPRAY | |
|---|---|
| Raw material/Brand or INCI name | % |
| GLYCEROL CAPRYLOCAPRATE | 5-20% |
| CYCLOPENTASILOXANE | 10-20% |
| DICAPRYLYL CARBONATE | 5-20% |
| TINOSORB S | 1-10% |
| TITANIUM OXIDE 100 | 10-20% |
| HECTORITE | 0-5% |
| ALPHA-TOCOPHEROL | 0-2% |
| LAURYL GLUCOSIDE-GLYSTEARATE | 0-10% |
| B4 PURIFIED WATER | Q.S. to 100% |
| CITRIC ACID | 0-2% |
| PENTYLENE GLYCOL | 0-5% |
| GLYCEROL | 0-5% |
| XANTHAN GUM | 0-2% |
| Extract of *Gynandropsis gynandra* | 0.01-10% |
| *ALOE VERA* | 0-1% |
| ZINC GLUCONATE | 0-1% |
| PRESERVATIVES | 0-2% |
| TINOSORB M | 1-10% |

| ANTI-ACNE EMULSION | |
|---|---|
| Raw material/Brand or INCI name | % |
| PEG 40 STEARATE | 1-5% |
| PEG 5 GLYCERYL STEARATE | 1-5% |
| CERESIN WAX | 1-5% |
| GLYCEROL MONOSTEARATE | 1-5% |
| SORBITAN STEARATE | 0-2% |
| CETYL ALCOHOL | 0-2% |
| DIMALATE ALCOHOL | 5-20% |
| VITAMIN E | 0-1% |
| VITAMIN B3 | 0-5% |
| LINOLEIC ACID | 0-1% |
| Extract of *Gynandropsis gynandra* | 0.01-10% |
| BUTYLENE GLYCOL | 1-5% |
| PIROCTOLAMINE | 0-1% |
| PRESERVATIVES | 0-1% |
| GLYCEROL | 1-10% |
| XANTHAN GUM | 0-1% |
| ZINC PCA | 0-2% |
| RICE STARCH | 1-5% |
| NYLON 6 | 0-2% |

-continued

ANTI-ACNE EMULSION

| Raw material/Brand or INCI name | % |
|---|---|
| POLYACRYLAMIDE GEL | 1-5% |
| VITAMIN B6 | 0-1% |
| FRAGRANCE | 0-1% |
| PURIFIED WATER | Q.S. to 100% |

ANTIDANDRUFF SHAMPOO

| Raw material/Brand or INCI name | % |
|---|---|
| PURIFIED WATER | Q.S. to 100% |
| LAUROAMPHOACETATE | 5-20% |
| COCOGLUCOSIDE | 5-20% |
| PEG 6000 DISTEARATE | 1-5% |
| PRESERVATIVES | 0-2% |
| VITAMIN F | 0-5% | extract of *Gynandropsis gynandra* (GG) at concentrations of 0.005%, 0.01% and 0.02% (w/v of active material) or with a reference inhibitor for 24 or 48 hours.

At the end of the treatment, the neutral lipids were quantified by measuring fluorescence after staining with Nile red. This measurement, expressed in relative fluorescence units (RFU) reflects the "de novo" synthesis of intracellular lipids by the sebocytes.

The results were analyzed statistically by one-factor analysis of variance (ANOVA) followed by a Dunnett's test.

Results and Conclusion:

The extract of GG strongly and significantly inhibited the production of lipids by sebocytes in basal condition (constitutive synthesis) and stimulated with acid arachidonic (Table 1).

These results show that the extract of GG is of interest in terms of regulating the production of sebum which increases in acne.

TABLE 1

Synthesis of lipids by sebocytes

| | | 24 HOURS | | 48 HOURS | |
|---|---|---|---|---|---|
| | | RFU (mean ± SEM) | Inhibition (%) | RFU (mean ± SEM) | Inhibition (%) |
| Sebocytes in basal state | Control | 29640.28 ± 1019.29 | | 97604.09 ± 3736.99 | |
| | 0.005% GG | 25440.10 ± 198.28 | 14 p < 0.01 | 74085.896 ± 1047.96 | 24 p < 0.05 |
| | 0.01% GG | 22893.63 ± 475.55 | 23 p < 0.001 | 46292.89 ± 2805.65 | 53 p < 0.001 |
| | 0.02% GG | 19276.25 ± 883.24 | 35 p < 0.001 | 43252.41 ± 1149.51 | 56 p < 0.001 |
| | Reference inhibitor | 29640.28 ± 1019.29 | 0 ns | 45229.89 ± 10406.07 | 54 p < 0.001 |
| Sebocytes stimulated by arachidonic acid | Arachidonic acid | 58393.80 ± 1667.47 | | 263211.67 ± 19744.67 | |
| | 0.005% GG | 54804.64 ± 654.07 | 6 ns | 209406.77 ± 5875.92 | 20 p < 0.05 |
| | 0.01% GG | 45644.06 ± 623.10 | 22 p < 0.001 | 108301.22 ± 4605.77 | 59 p < 0.001 |
| | 0.02% GG | 30823.73 ± 1310.56 | 47 p < 0.001 | 43726.41 ± 1809.07 | 83 p < 0.001 |
| | Reference inhibitor | 44282.33 ± 645.11 | 24 p < 0.001 | 91723.64 ± 696.97 | 65 p < 0.001 |

-continued

ANTIDANDRUFF SHAMPOO

| Raw material/Brand or INCI name | % |
|---|---|
| PIROCTONE OLAMINE | 0-2% |
| Extract of *Gynandropsis gynandra* | 0.01-10% |
| ZINC PYRITHIONE | 0-1% |
| PH ADJUSTER | 0-1% |
| SEQUESTRANT | 0-1% |
| FRAGRANCE | 0-1% |

EXAMPLE 5

Biological Activity of the Extract of *Gynandropsis gynandra*

A. Biological Activity in Acne

A.1. Action on Hyperseborrhea: Inhibition of Lipid Synthesis by Sebocytes

Materials and Methods:

Human sebocytes (SZ95 cell line), stimulated or not stimulated with 50 μM arachidonic acid, were treated with the A.2. Action on the Aggravating Factors of Acne 1. Keratinocytes Model Materials and Methods:

Human keratinocytes (NCTC-2544 cell line) were preincubated or not (control) with the extract of *Gynandropsis gynandra* (GG) at concentrations of 0.01% and 0.02% (w/v of active material) or the reference molecules ($10^{-7}$ M dexamethasone, $10^{-6}$ M indomethacin) for 24 hours. The cells were then treated with 0.1 μg/ml phorbol myristate acetate (PMA) for 24 hours, always in the presence of GG or the references.

At the end of the treatment, the quantities of interleukin 8 (IL8) and prostaglandin E2 (PGE2) secreted were measured by ELISA in the culture supernatants. The results were analyzed statistically by a Student's t-test.

Results and Conclusion:

The extract of GG strongly and significantly inhibited the production of aggravating mediators of acne IL8 and PGE2 stimulated by PMA in keratinocytes (Table 2).

The extract of GG modulates early aggravating factors of acne.

TABLE 2

Production of IL8 and PGE2 by keratinocytes

|  | IL8 (ng/ml) | Inhibition |
|---|---|---|
| Control cells | 0.1 ± 0.0 | |
| 0.1 µg/ml PMA | 50.1 ± 1.8 | |
| $10^{-7}$ M Dexamethasone | 7.4 ± 0.8 | 85% p < 0.001 |
| 0.01% GG | 28.3 ± 0.5 | 44% p < 0.001 |
| 0.02% GG | 17.6 ± 0.5 | 65% p < 0.001 |
|  | PGE2 (ng/ml) | |
| Control cells | 0.039 ± 0.0 | |
| 0.1 µg/ml PMA | 138.4 ± 10.6 | |
| $10^{-6}$ M Indomethacin | 0.039 ± 0.0 | 100% p < 0.001 |
| 0.01% GG | 24.1 ± 3.0 | 83% p < 0.001 |
| 0.02% GG | 9.8 ± 0.0 | 93% p < 0.001 |

2. Modulation of the Effect of *P. acnes* on Keratinocytes

Materials and Methods:

Human keratinocytes (HaCaT cell line) were preincubated for 48 hours in the presence of the extract of *Gynandropsis gynandra* (GG) at concentrations of 0.0005%, 0.002%, 0.008% and 0.031% (w/v of active material) or the reference inhibitor, nicotinamide.

The keratinocytes were then stimulated by incubation for 18 hours with a bacterial suspension of *P. acnes* (strain ATCC6919).

At the end of incubation, the quantity of IL8 produced by the keratinocytes was measured in the culture supernatants by an ELISA technique.

The results were analyzed statistically by a Student's t-test: ns (not significant) p>0.05, *p<0.05, p<0.01, *p<0.001.

Results and Conclusion:

FIG. 1 represents the production of IL8, in pg/ml, by keratinocytes stimulated by *P. acnes*, as a function of the concentration of active agent in percentage.

The extract of GG significantly inhibited the production of IL8 induced by *P. acnes* on keratinocytes (FIG. 1).

The extract of GG modulates the impact of *P. acnes* in the physiopathology of acne.

3. Stimulation of the Expression of Antimicrobial Peptides

Materials and Methods:

Normal human keratinocytes, cultured in $Ca^{++}$-enriched medium, were treated for 24 hours with the extract of *Gynandropsis gynandra* (GG) at a concentration of 0.005% (w/v of active material).

At the end of the treatment, the gene expression of antimicrobial peptides (beta-defensins 2 and 3-hBD2, hBD3- and cathelicidin LL37) was analyzed by quantitative real-time RT-PCR.

The results were analyzed statistically by one-factor ANOVA followed by a Dunnett's test: ns (not significant) p>0.05; p<0.01; *p<0.001.

Results and Conclusion:

The extract of GG stimulated the expression of antimicrobial peptides by the keratinocytes (Table 3).

Thus, the extract of GG makes it possible to limit bacterial colonization of the skin and thus to limit the pathogenicity related to *P. acnes*.

TABLE 3

Gene expression of antimicrobial peptides hBD2, hBD3 and LL37 in keratinocytes (relative quantity)

|  | HBD2 | HBD3 | LL37 |
|---|---|---|---|
| Control cells | 1.00 | 1.00 | 1.00 |
| 0.005% GG | 2.70 | 1.85 | 1.51 |
|  | (+170% **) | (+85% ***) | (+51% ns) |

4. Modulation of Neutrophil Migration

The neutrophil plays an important role in the physiopathology of acne. It is present in a high quantity in acneic skin notably due to the many chemotactic substances produced by *P. acnes*.

Materials and Methods:

Human neutrophils were pretreated for 30 minutes with the extract of *Gynandropsis gynandra* at concentrations of 0.001% and 0.002% (w/v of active material) or with a reference inhibitor.

The cells were then deposited in the Transwell® migration system: the pretreated neutrophils were deposited in inserts positioned on a receiving plate containing the chemoattractant fMLP (N-formyl-Met-Leu-Phe) at a concentration of 1 µM.

After 2 hours of incubation, the number of neutrophils having migrated was evaluated by measuring the enzymatic activity of lactate dehydrogenase (LDH).

The results were analyzed statistically by a Student's t-test.

Results and Conclusion:

Neutrophil migration was significantly inhibited by the extract of GG (Table 4).

The extract of GG thus prevents the recruitment of neutrophils in the skin described in acne.

TABLE 4

Migration of neutrophils

|  | Migration (%) | Inhibition in relation to cells stimulated by fMLP |
|---|---|---|
| Control cells | 1.89 ± 0.2 | |
| fMLP | 25.1 ± 3.02 | |
| Inhibitor | 6.4 ± 0.26 | −74% p < 0.01 |
| 0.001% GG | 8.65 ± 0.24 | −66% p < 0.01 |
| 0.002% GG | 14.05 ± 1.26 | −44% p < 0.05 |

5. Inhibition of the Production of Leukotriene B4 by Neutrophils

Leukotriene B4 is produced and released in large quantities by the neutrophil, it plays a role in acne lesions and induces the secretion of sebum.

Materials and Methods:

Human neutrophils were preincubated for 15 minutes in the presence of the extract of *Gynandropsis gynandra* (GG) at concentrations of 0.002% and 0.008% (w/v of active material).

The cells were then stimulated by adding 1 mg/ml opsonized zymosan.

After 10 minutes of incubation, the leukotriene B4 (LTB4) released by the cells was assayed in the cell supernatants by an ELISA technique.

The results were analyzed statistically by a Student's t-test.

Results and Conclusion:

The extract of GG significantly inhibited the production of LTB4 induced by opsonized zymosan on the neutrophils (Table 5).

Thus, the extract of GG modulates the impact of the neutrophil and LTB4 in acne.

TABLE 5

Production of leukotriene B4 by neutrophils

|  | LTB4 (pg/ml) | Inhibition |
| --- | --- | --- |
| Control cells | 81.45 ± 7.16 |  |
| Stimulated cells | 439.32 ± 3.01 |  |
| 0.002% GG | 199.17 ± 4.83 | −54% p < 0.001 |
| 0.008% GG | 220.91 ± 1.75 | −49% p < 0.001 |

6. Inhibition of the Release of Histamine by Mastocytes

Histamine can alter the production of sebum. Indeed, sebocytes (constitutive cells of the sebaceous gland, responsible for the production of sebum) have histamine receptors on their surface.

Materials and Methods:

Mastocytes were preincubated for 30 minutes in the presence of the extract of *Gynandropsis gynandra* (GG) at a concentration of 0.08% (w/v of active material) or 10 Mm of calcium (reference inhibitor of histamine release).

The mastocytes were then stimulated with 10 µM of substance P for 15 minutes. At the end of incubation, the histamine released was quantified by ELISA.

The results were analyzed statistically by a Student's t-test.

Results and Conclusion:

The extract of GG strongly and significantly inhibited the release of histamine by mastocytes stimulated by substance P (Table 6).

The extract of GG modulates the effect of histamine in acne.

TABLE 6

Release of histamine by mastocytes

|  | Histamine (ng/ml) | Inhibition |
| --- | --- | --- |
| Control | 20.1 ± 1.9 |  |
| Substance P | 142.5 ± 9.6 |  |
| 10 nM Calcium | 21.8 ± 1.0 | −85% p < 0.01 |
| 0.08% GG | 12.3 ± 1.3 | −91% p < 0.01 |

A.3. Oxidative Stress

In acne, there is an oxidative stress characterized by a high production of oxygen free radicals (OFR). The severity of acne is correlated with this quantity of OFR.

Furthermore, squalene (lipid constituent of sebum) is oxidized in acne.

1. Antioxidant Effect

Materials and Methods:

Normal human keratinocytes were treated for 24 hours with the extract of *Gynandropsis gynandra* (GG) at a concentration of 0.032% (w/v of active material) or with 10 µg/ml of vitamin C (reference antioxidant) before incorporation of the H2DCF-DA probe (incubation for 45 minutes).

The keratinocytes were then stimulated with 100 µM of hydrogen peroxide ($H_2O_2$) for 20 minutes.

The production of reactive oxygen species (ROS) was evaluated by measuring fluorescence.

The results were analyzed statistically by a Student's t-test.

Results and Conclusion:

The extract of GG inhibited the production of ROS by keratinocytes in response to oxidative stress induced by $H_2O_2$ (Table 7), and it thus has an antioxidant effect.

TABLE 7

Production of ROS in keratinocytes treated with $H_2O_2$

|  | ROS (fluorescence units) | Inhibition |
| --- | --- | --- |
| Stimulated cells ($H_2O_2$) | 1474.5 ± 93.32 |  |
| Reference (vitamin C) | 992.83 ± 93.96 | 33% p < 0.05 |
| 0.032% GG | 981.33 ± 132.52 | 33% p < 0.05 |

2. Protection Against Lipid Peroxidation

Materials and Methods:

Cells of the Jurkat cell line were preincubated for 45 minutes in the presence of the extract of *Gynandropsis gynandra* (GG) at a concentration of 0.02% (w/v of active material) or 100 µM of BHT (reference) and in the presence of the fluorescent probe 011-fluorine, specific for lipid peroxidation.

The cells were then irradiated by UVA+B and then incubated for 30 minutes in the presence of GG or BHT.

At the end of incubation, the quantity of lipid peroxides was evaluated by a flow cytometry analysis of fluorescence intensity (inversely proportional to oxidation).

The results were analyzed statistically by a Student's t-test.

Results and Conclusion:

The extract of GG significantly protected the cells against lipid peroxidation induced by UV irradiation (Table 8).

TABLE 8

UV-induced lipid peroxidation

|  | Lipid peroxides (% of irradiated control) | Protection (%) |
| --- | --- | --- |
| Irradiated cells (UV) | 100 |  |
| 100 µM BHT | 64 | 49% p < 0.01 |
| 0.02% GG | 83 | 23% p < 0.05 |

A.4. Healing Action: Stimulation of Keratinocyte Migration

Acne lesions can lead to the formation of ugly scars. Therefore, acne treatments may be accompanied by a pro-healing action.

Materials and Methods:

An artificial wound was prepared on a monolayer of normal human keratinocytes.

The cells were stained with calcein and then incubated for 72 hours in the presence of the extract of *Gynandropsis gynandra* (GG) at concentrations of 0.001% and 0.005% (w/v of active material) or the reference (10 ng/ml of EGF).

At 0, 24, 48 and 72 hours, keratinocyte migration was monitored by microphotography and was quantified by measuring the surface area of the wound.

Figure 2:
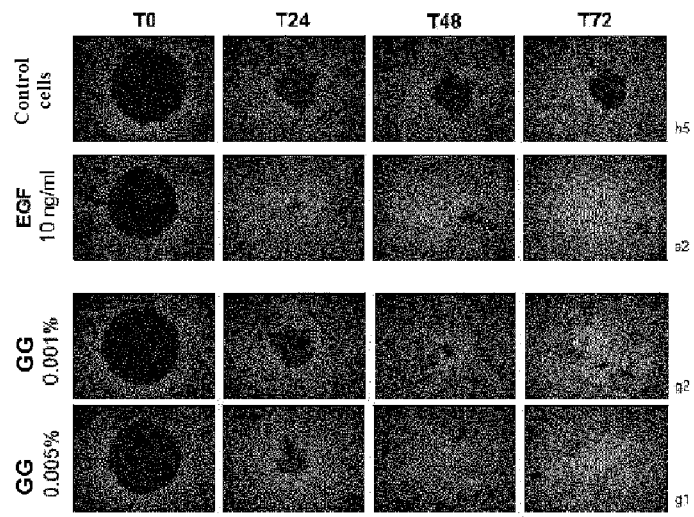
FIG. 2 represents photographs of control cells or cells incubated in the presence of the extract of *Gynandropsis gynandra* (GG) at concentrations of 0.001% and 0.005% (w/v of active material) or the reference (10 ng/ml of EGF) at 0 (TO), 24 (T24), 48 (T48) and 72 hours (T72), with TO being the moment the wound was prepared.

FIG. 2 represents photographs of control cells or cells incubated in the presence of the extract of *Gynandropsis gynandra* (GG) at concentrations of 0.001% and 0.005% (w/v of active material) or the reference (10 ng/ml of EGF) at 0 (T0), 24 (T24), 48 (T48) and 72 hours (T72), with T0 being the moment the wound was prepared.

The results were analyzed statistically by a Student's t-test.

Results and Conclusion:

The extract of GG significantly stimulated the migration of keratinocytes (Table 9, FIG. 2) with total coverage of the wound after 48 hours.

The extract of GG thus supports the process of reepithelialization during cutaneous healing.

TABLE 9

Evaluation of keratinocyte migration

| | Migration area (percent of wound covered) | | |
|---|---|---|---|
| | 24 h | 48 h | 72 h |
| Control cells | 62 | 68 | 71 |
| Reference (EGF) | 95 ($p < 0.001$) | 99 ($p < 0.001$) | 100 ($p < 0.001$) |
| 0.001% GG | 68 (ns) | 96 ($p < 0.001$) | 99 ($p < 0.001$) |
| 0.005% GG | 72 (ns) | 99 ($p < 0.001$) | 99 ($p < 0.001$) |

B. Other Biological Activities

B.1. Inhibition of Lipogenesis in Adipocytes

Materials and Methods:

Normal human adipocytes were incubated for 1 hour in the presence of the extract of *Gynandropsis gynandra* (GG) at a concentration of 0.02% (w/v of active material) or the reference (20 μM of cerulenin). After incubation, the radioactive label [$^{14}$C]-acetate was added and the samples were incubated overnight.

At the end of incubation, the lipids were extracted and the radioactivity incorporated (corresponding to the lipogenesis) was measured by liquid scintillation.

The results were analyzed statistically by a Student's t-test.

Results and Conclusion:

The extract of GG significantly inhibited the neosynthesis of lipids by adipocytes (Table 10).

Thus, this extract has a slimming effect.

TABLE 10

Evaluation of lipogenesis in adipocytes

| | Incorporation of acetate (cpm) | Inhibition |
|---|---|---|
| Control cells | 32895 ± 1358 | |
| Reference (cerulenin) | 14934 ± 671 | 55% $p < 0.001$ |
| 0.02% GG | 26573 ± 227 | 19% $p < 0.05$ |

B.2. Increase in Melanin Production by Melanocytes

Materials and Methods:

Normal human epidermal melanocytes were cultured for 240 hours in the presence of the extract of *Gynandropsis gynandra* (GG) at concentrations of 0.002% and 0.01% (w/v of active material) and $10^{-7}$ M of NDP-MSH (stimulation of melanin synthesis).

After incubation, melanin was extracted from the cells and was quantified by spectrophotometry.

The results were analyzed statistically by a Student's t-test.

Results and Conclusion:

The extract of GG significantly stimulated and potentiated the effect of NDP-MSH on the production of melanin (Table 11).

The extract thus has a pro-pigmenting effect.

TABLE 11

Melanin production by melanocytes

| | Melanin (μl/ml) | Stimulation |
|---|---|---|
| Control cells | 13.0 ± 1.1 | |
| Stimulated control (NDP-MSH) | 27.1 ± 0.9 | +108% $p < 0.001$ |
| 0.002% GG | 35.1 ± 0.3 | +170% $p < 0.01$ |
| 0.01% GG | 41.2 ± 0.5 | +217% $p < 0.001$ |

B.3. Screening of Activity on Endothelial Cells

Materials and Methods:

Human microvascular endothelial cells were treated with the extract of *Gynandropsis gynandra* (GG) at concentrations of 0.01% and 0.02% (w/v of active material) for 24 hours.

After incubation, the gene expression of various markers was analyzed by quantitative real-time RT-PCR using a PCR array.

Results and Conclusion:

The results of the screening on endothelial cells made it possible to show that the extract of *Gynandropsis gynandra* (Table 12):

Inhibits the gene expression of proangiogenic molecules: placental growth factor (PGF), platelet derived growth factor (PDGF) subunit B and vascular endothelial growth factor receptor-3 (VEGFR3).

Stimulates the expression of antiangiogenic molecules: thrombospondin-1 and endostatin.

Stimulates the expression of molecules involved in vasoconstriction: calmodulin and endothelin-1.

These effects are in favor of an inhibition of angiogenesis and vascular dilatation, and thus show an anti-redness activity of GG.

Stimulates the expression of molecules involved in vessel strength and elasticity: alpha smooth muscle actin (αSMA) and troponin 1.

Stimulates the expression of defense molecules: heme oxygenase-1 (protective role by preventing free heme from participating in pro-oxidative reactions) and thioredoxin (repair of oxidative damage to proteins).

These effects are in favor of an activity of strengthening and protecting vascular walls by GG.

TABLE 12

Screening of activity via PCR array on endothelial cells

| | Gene expression (relative quantity in % in relation to control cells) | | |
|---|---|---|---|
| | Control cells | 0.01% GG | 0.02% GG |
| Proangiogenic growth factors | | | |
| PGF | 100 | 64 | 53 |
| PDGFB | 100 | 84 | 62 |
| VEGFR3 | 100 | 57 | 65 |
| Antiangiogenic molecules | | | |
| Thrombospondin-1 | 100 | 148 | 183 |
| Endostatin | 100 | 112 | 220 |
| Vasoconstriction | | | |
| Calmodulin | 100 | 120 | 165 |
| Endothelin-1 | 100 | 127 | 169 |
| Vessel strengthening/elasticity | | | |
| αSMA | 100 | 127 | 183 |
| Troponin-1 | 100 | 177 | 184 |
| Defense/response to oxidative stress | | | |
| Heme oxygenase-1 | 100 | 185 | 320 |
| Thioredoxin | 100 | 126 | 171 |

The invention claimed is:

1. A cosmetic method for improving the condition or appearance of skin and/or keratinous appendages and/or mucous membranes comprising:

applying to the skin and/or keratinous appendages and/or mucous membranes of a subject in need thereof a composition comprising an effective amount of an extract from the above ground parts of *Gynandropsis gynandra*, wherein the extract includes at least 3% polyphenols by weight, expressed in gallic acid equivalents in relation to the dry weight of the extract, and wherein the extract is obtained by solid-liquid extraction of the above ground parts of *Gynandropsis gynandra* in a binary mixture of water and a solvent selected from ethanol, glycerol, and glycol.

2. The method of claim 1, wherein the skin and/or keratinous appendages and/or mucous membranes exhibit redness, acne, an acneic tendency, or dandruff.

3. The method of claim 1, wherein the extract is an extract of *Gynandropsis gynandra* leaves.

4. The method of claim 1, wherein the water in the binary mixture is present in an amount of 10% to 50%.

5. The method of claim 1, wherein the glycol is propanediol.

6. The method of claim 4, wherein the glycol is propanediol.

7. The method of claim 1, wherein the skin is afflicted with acne.

8. The method of claim 1, wherein the skin and/or keratinous appendages and/or mucous membranes are sensitive or damaged by the environment.

9. A method for inhibiting and/or treating at least one disorder related to hyperseborrhea in a subject in need thereof comprising:

administering to said subject a composition comprising an effective amount of an extract from the above ground parts of *Gynandropsis gynandra*, wherein the extract includes at least 3% polyphenols by weight, expressed in gallic acid equivalents in relation to the dry weight of the extract, and wherein the extract is obtained by solid-liquid extraction of the above ground parts of *Gynandropsis gynandra* in a binary mixture of water and a solvent selected from ethanol, glycerol, and glycol.

10. The method of claim 9, wherein said disorder is seborrheic dermatitis.

11. The method of claim 9, wherein said composition is administered by topical external route.

* * * * *